United States Patent [19]

Berndt et al.

[11] Patent Number: 5,427,920
[45] Date of Patent: Jun. 27, 1995

[54] METHODS AND APPARATUS FOR DETECTING BIOLOGICAL ACTIVITIES IN A SPECIMEN

[75] Inventors: Klaus W. Berndt, Stewartstown, Pa.; Paul G. Gladnick; Dolores M. Berger, both of Baltimore, Md.

[73] Assignee: Becton Dickinson and Company, Franklin Lakes, N.J.

[21] Appl. No.: 215,957

[22] Filed: Mar. 18, 1994

Related U.S. Application Data

[63] Continuation of Ser. No. 874,324, Apr. 24, 1992, abandoned.

[51] Int. Cl.⁶ .................. C12Q 1/04; C12M 1/34; G01N 33/48; G01N 21/00
[52] U.S. Cl. .......................... 435/34; 435/32; 435/291; 435/808; 356/39; 356/339; 356/436; 356/342
[58] Field of Search ............... 435/4, 32, 33, 34, 29, 435/39, 40, 287, 300, 291, 808; 422/82.05, 82.09; 436/164; 356/39, 342, 339, 436, 338, 441, 442, 432, 433, 434

[56] References Cited

U.S. PATENT DOCUMENTS

| | | | |
|---|---|---|---|
| 3,837,746 | 9/1974 | Acker et al. | 250/575 |
| 3,880,526 | 4/1975 | Kobayashi et al. | 356/442 |
| 3,916,197 | 10/1975 | Fulwyler | 250/575 |
| 4,152,213 | 5/1979 | Ahnell | 435/34 |
| 4,324,556 | 4/1982 | Robertson et al. | 422/82.09 |
| 4,492,462 | 1/1985 | Pross et al. | 359/39 |
| 4,653,907 | 3/1987 | Freundlich | 356/39 |
| 4,945,060 | 7/1990 | Turner et al. | 435/291 |
| 4,999,513 | 3/1991 | Ito et al. | 250/575 |
| 5,073,029 | 12/1991 | Eberly et al. | 422/82.05 |
| 5,082,628 | 1/1992 | Andreotti et al. | 422/82.08 |
| 5,155,019 | 10/1992 | Sussman et al. | 422/82.05 |
| 5,164,597 | 11/1992 | Lodder | 356/341 |
| 5,187,368 | 2/1993 | Galante et al. | 250/341 |

OTHER PUBLICATIONS

Thurman C. Thorpe, et al., "BacT/Alert: an Automated Colorimetric Microbial Detection System," *Journal of Clinical Microbiology*, Jul. 1990, pp. 1608–1612.

M. S. Patterson et al., "Photodynamic Therapy: Mechanisms," *SPIE*, vol. 1065 (1989), pp. 115–122.

*Primary Examiner*—Robert J. Warden
*Assistant Examiner*—Theresa T. Snider
*Attorney, Agent, or Firm*—Alan W. Fiedler

[57] ABSTRACT

Methods and apparatus for detecting biological activities in a specimen such as blood are disclosed. The present invention provides a system whereby the intensity of light with a wavelength within the range of about 600 nm to 800 nm introduced into a sample at a first location is measured as it reemerges at a second location. A significant change in the intensity of the reemerging light indicates the presence of biological activity. Preferably, the intensity is also measured at a fourth location, or alternatively, a second light source is disposed at a third location to permit comparative intensity data to be collected. These data are useful in partially identifying the types of microorganisms present in the sample. In preferred embodiments, light emitting diodes are used as the light sources and multiplexed to a plurality of samples. These signals are either detected using photodetectors and demultiplexed, or are collected using fiber-optic light guides and fed to a photomultiplier tube which generates an intensity signal. In either embodiment, the intensity signal is preferably amplified, digitized and stored in a computer.

21 Claims, 5 Drawing Sheets

METHODS AND APPARATUS FOR DETECTING BIOLOGICAL ACTIVITIES IN A SPECIMEN

This application is a continuation of application Ser. No. 07/874,324, filed Apr. 24, 1992, now abandoned.

The present invention relates to non-invasive methods and apparatus for detecting biological activities in a specimen such as blood by measuring the absorption and scattering of light, and in particular to systems wherein the specimen and a culture medium are introduced into a sealable container and exposed to conditions enabling metabolic processes to take place.

BACKGROUND OF THE INVENTION

Usually, the presence of biologically active agents such as bacteria in a patient's body fluid, and especially in blood, is determined using blood culture vials. A small quantity of blood is injected through an enclosing rubber septum into a sterile vial containing a culture medium. The vial is typically incubated at 37° C. and monitored for bacterial growth.

Common visual inspection involves monitoring the turbidity or observing eventual color changes of the liquid suspension. Known instrumented methods detect changes in the carbon dioxide content of the culture bottles, which is a metabolic byproduct of the bacterial growth. Monitoring the carbon dioxide content can be accomplished by methods well established in the art, such as radiochemical (e.g., BACTEC®, Becton-Dickinson, Franklin Lakes, N.J., U.S.A.), infrared absorption at a carbon dioxide spectral line (e.g., NR-BACTEC®, Becton-Dickinson, Franklin Lakes, N.J., U.S.A.), or pressure/vacuum measurement such as those disclosed in U.S. Pat. No. 4,152,213—Ahnell. However, all these methods require invasive procedures which result in the well-known problem of cross-contamination between different vials. For purposes of this application, the term invasive implies that the confines of the sample container must be entered in order to determine if bacteria are present, e.g., a probe is inserted into a sealed vial. In the first two methods mentioned above, the headspace gas must be removed for analysis. In the case of vacuum/pressure measurement, while pressure is measured in a closed vial, any temperature change within the vial headspace also generates a pressure change that is not related to biological activity.

Therefore, an additional headspace temperature measurement is required in order to distinguish between biological and temperature-generated pressure effects. Non-invasive headspace temperature monitoring, however, represents a difficult problem, and no satisfactory solutions are at hand. Additionally, some microorganisms can produce high pressure values while others produce relatively low or negligible ones. Thus, any pressure sensors used must be sensitive enough to allow detection of small changes in pressure while also being capable of safely measuring high pressure values. These two requirements are often mutually exclusive depending on the type of pressure sensor technology used. Thus far none of the systems known in the prior art permit the rapid and reliable detection of a wide variety of bacteria.

Recently, non-invasive methods have been developed involving chemical sensors disposed inside the vial. These sensors respond to changes in the carbon dioxide concentration by changing their color or by changing their fluorescence intensity. See, e.g., Thorpe, et al. "BacT/Alert: an Automated Colormetric Microbial Detection System" J. Clin. Microb., July 1990, pp. 1608–12 and U.S. Pat. No. 4,945,060. These techniques are based on light intensity measurements and require spectral filtering in the excitation and/or emission signals. This means that errors can occur if any of the light source, the photodetector, the filters, or the sensor show aging effects over time which would vary the intensity response.

The disadvantage of such intensity-based methods can be overcome by utilizing a modulated excitation signal in combination with fluorescent sensors that change fluorescent their decay time with changing carbon dioxide concentration. In such a device, light intensity measurement is replaced with time measurement, and intensity changes and the related variations in sensor sensitivity have no impact upon its operation. However, current fluorescent decay time sensors require high-brightness, short-wavelength light sources (550 nm or shorter) that are intensity-modulated at very high frequencies (typically about 100 MHz). Thus, for example, such a system might use a 5-mW green HeNe laser (543.5 nm), externally modulated by means of an acousto-optic light modulator, the operation of which is understood by those of ordinary skill. However, it will be realized that such a laser/modulator combination is rather expensive, requiring that the samples be moved to the laser, instead of having one light source at each sample. Such an instrument would therefore by necessity have a complicated mechanism for effecting the transportation of the individual samples to the light source and the time interval between successive measurements for each sample would be relatively long. It appears unlikely that high-brightness short-wavelength semiconductor diode lasers will be developed in the near future. Thus, even such an improved system would suffer serious practical shortcomings.

It is therefore an object of the present invention to overcome the limitations of the prior art described above by providing methods and apparatus for detecting biological activities in a specimen such as blood, that are non-invasive and that do not require chemical sensors or any additives within the blood culture vial. It is another object of this invention to provide a system that does not require high-brightness, short-wavelength light sources. Another object of the present invention is to provide methods and apparatus that are safe against potentially extreme high pressure values and that are not sensitive to headspace temperature changes. A still further object of the present invention is to provide a system that is simple and inexpensive, so that each vial can be monitored continuously, thus allowing the construction of diagnostic instruments containing a plurality of stationary vials.

SUMMARY OF THE INVENTION

According to the present invention, these and other objects are achieved by introducing a sample, most preferably a culture medium and blood specimen, into a sample vial, injecting light of high intensity and of a wavelength in the region 600 nm to 800 nm into the vial containing the sample, and measuring the intensity of light reemerging from the vial. Preferably, the intensity is measured at at least two positions, and most preferably at a position on the vial side opposite to the light injection area, and at a second position approximately one-half of this distance. In certain embodiments a back scatter detector is also provided at a location approximately adjacent the point at which the light is injected.

A first preferred embodiment of the apparatus of the present invention comprises a plurality of sealed blood culture vials, each containing a culture medium and a blood specimen, arranged within an incubator which maintains a temperature of about 37° C. in order to allow for optimum growth conditions. The apparatus also comprises a DC power supply connected to the input of a multiplexer that is controlled by a computer and sequentially directs a DC signal to each of a plurality of light sources at least one of which is arranged on a side of each vial. In a preferred embodiment, the light sources are light emitting diodes.

At two positions on each vial approximately 180° and approximately 90° away from the location of the light source, large-area photodiode detectors that measure the intensity of the received electromagnetic radiation are disposed. The detectors, however, may be located at other positions and will still function in accordance with the present invention. The intensity measured by each photodiode detector is transmitted as an analog signal to a demultiplexer that is also controlled by the computer and creates an output that is preferably subsequently amplified and fed to an analog-to-digital converter to create a digital intensity signal. Finally, the digital intensity signal is transmitted to the computer and intensity data are recorded.

In operation, the computer controls the multiplexer in such a way that a first light source is energized. The computer then directs the demultiplexer to serially activate the two inputs connected to the two photodiode detectors located on each vial as the light source is activated. The two photocurrents are serially measured and the data are stored in the computer memory. The light source on the first vial is then turned off, and the same procedure is repeated with all remaining vials. After a first cycle involving all the vials is completed, the measuring procedure is started again, and repeated continuously.

In a second preferred embodiment of the apparatus of the present invention, the photodiodes are replaced with two fiber-optic light guides arranged on each vial. The light guides are disposed at first and second positions similar to the positions of the photodiodes of the first embodiment described above, e.g., 90° and 180° relative to a single light source although other spacings are also useful. The outputs of the light guides are fed to a first and a second large-area photomultiplier tube, the outputs of which are also connected to the computer. In this embodiment no de-multiplexer is required, since the large-area photomultipliers act as a parallel-processing device. The separation between the two detector signals is accomplished by utilizing two identical signal channels, i.e., two photomultipliers, two preamplifiers, and two analog-to-digital converters.

Another embodiment of the apparatus of the present invention replaces the single light source with two light sources preferably disposed adjacent each vial in positions similar to those used for the detectors, i.e., preferably about 90° apart. A single photodetector is located such that it is preferably about 180° from a first light source and 90° away from the second light source. As described above with reference to the first embodiment, a multiplexer is used to serially excite the light sources and a demultiplexer is connected to the output of each photodiode detector. An advantage of this embodiment is that it uses half as many photodiode detectors by using twice as many of the less expensive light sources as the other embodiments.

Another embodiment of the apparatus of the present invention utilizes two light sources and a single fiber-optic light guide. The two sources are arranged as described immediately above and the light guide is preferably positioned 90° and 180° respectively from these two sources.

DETAILED DESCRIPTION OF THE PREFERRED EMBODIMENTS

It has been found that biological activities within a blood culture medium, such as bacterial growth processes, will result in a change in the reemerging intensities of light introduced into the medium. Therefore, biological activities such as bacterial growth can be detected by monitoring the reemerging light intensities. Because the photocurrent measurement per vial can be performed relatively quickly, frequent measurement of each vial is possible, which is a necessary condition to allow for an advantageously short bacterial detection time.

Figure 1:
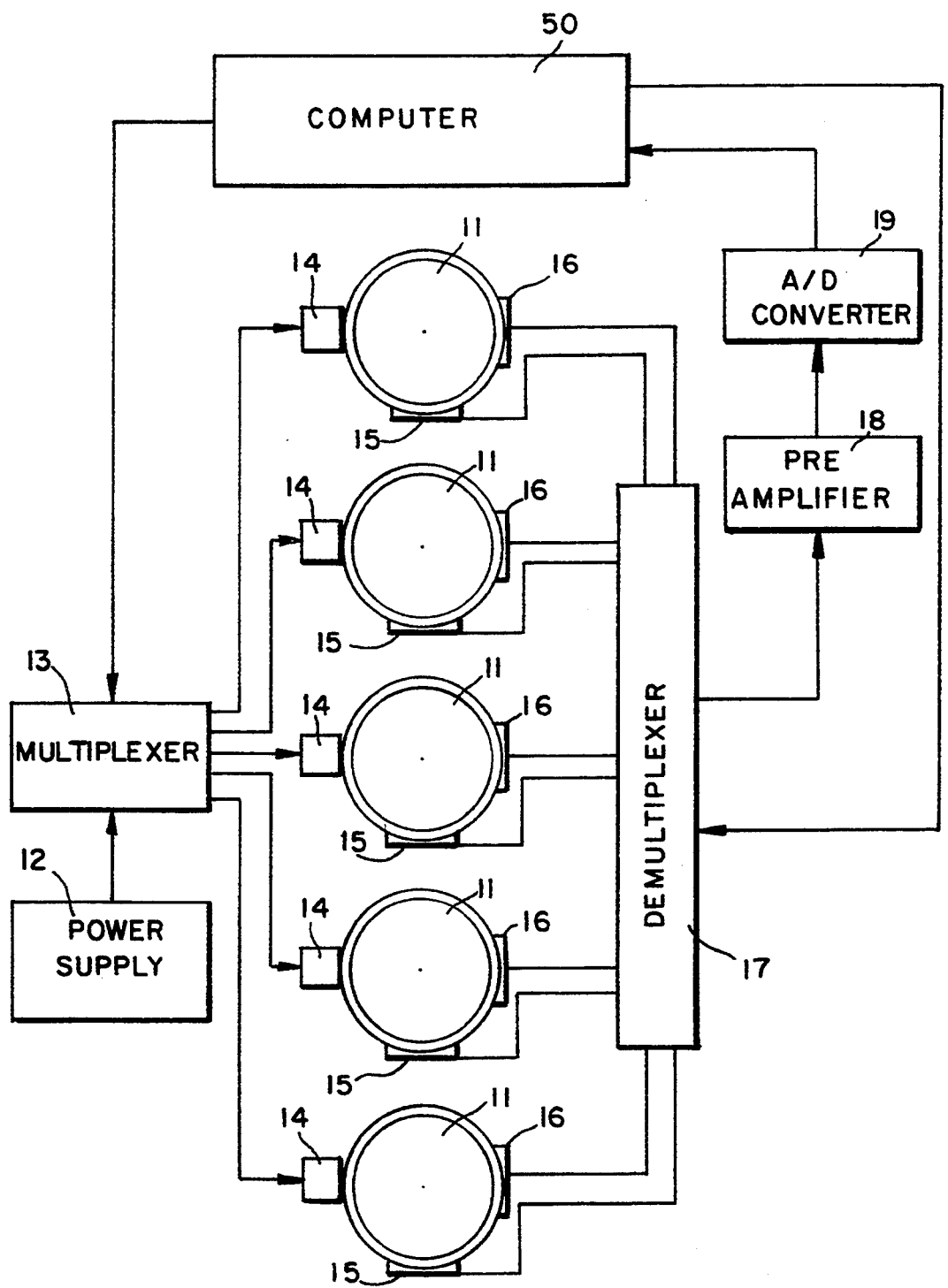
FIG. 1 schematically depicts an apparatus for detecting biological activities in a specimen made in accordance with the present invention that uses two photodiode detectors and one light source per sample vial.

A first embodiment of a detection apparatus embodying the principles and concepts of the present invention is depicted schematically in FIG. 1. The apparatus preferably comprises a plurality of sample vials 11, that are preferably sealed with a septum and contain a medium/blood mixture. A DC power supply 12 is connected to the input of a multiplexer 13 which is controlled by a computer 50. The multiplexer 13 directs a DC signal to light sources 14 that are arranged on one side of each vial 11. At two positions approximately 90° and approximately 180° away from the light source 14, the detectors 15,16 are arranged on each vial 11. The detectors 15,16 are preferably comprised of large area photodiodes and are connected to a demultiplexer 17 that is also controlled by the same computer 50 as the multiplexer 13. The analog output signal of the demultiplexer 17 is connected to a preamplifier 18, and its output is fed to an analog-to-digital converter 19. Finally, the digital output signal of the analog-to-digital converter 19 is connected to the computer 50 that includes a means for storing data. Those of ordinary skill will be generally familiar with the operation and parameters involved in selecting the above described components.

In operation, the computer 50 controls the multiplexer 13 such that a first light source 14 is turned on. The computer 50 then directs the de-multiplexer 17 to activate, in a serial mode of operation, the two inputs connected with the two photodiodes 15,16 located on the first vial 11 corresponding to where the first light source 14 is turned on. The two photocurrents are serially measured, and the data are stored in the memory of the computer 50 after being amplified and converted to digital form. The first light source 14 is then turned off, and the same procedure is repeated step by step with all remaining vials 11 by sequentially activating each light source 14. After the first cycle involving all vials 11 is complete, the procedure is started again, and repeated continuously.

Thus, this embodiment of the present invention, as well as those described below, permits each vial 11 to remain stationary while bacteria are being detected. Additionally, as noted above, since a plurality of samples are sequentially checked and the cycle repeated, the detection time is highly accurate. Although five sample vials 11 are illustrated, it will be understood that the present invention is directed to embodiments capable of handling hundreds of sample vials at once. At present, a preferred embodiment of this invention will be able to test 240 vials at one time.

Figure 2:
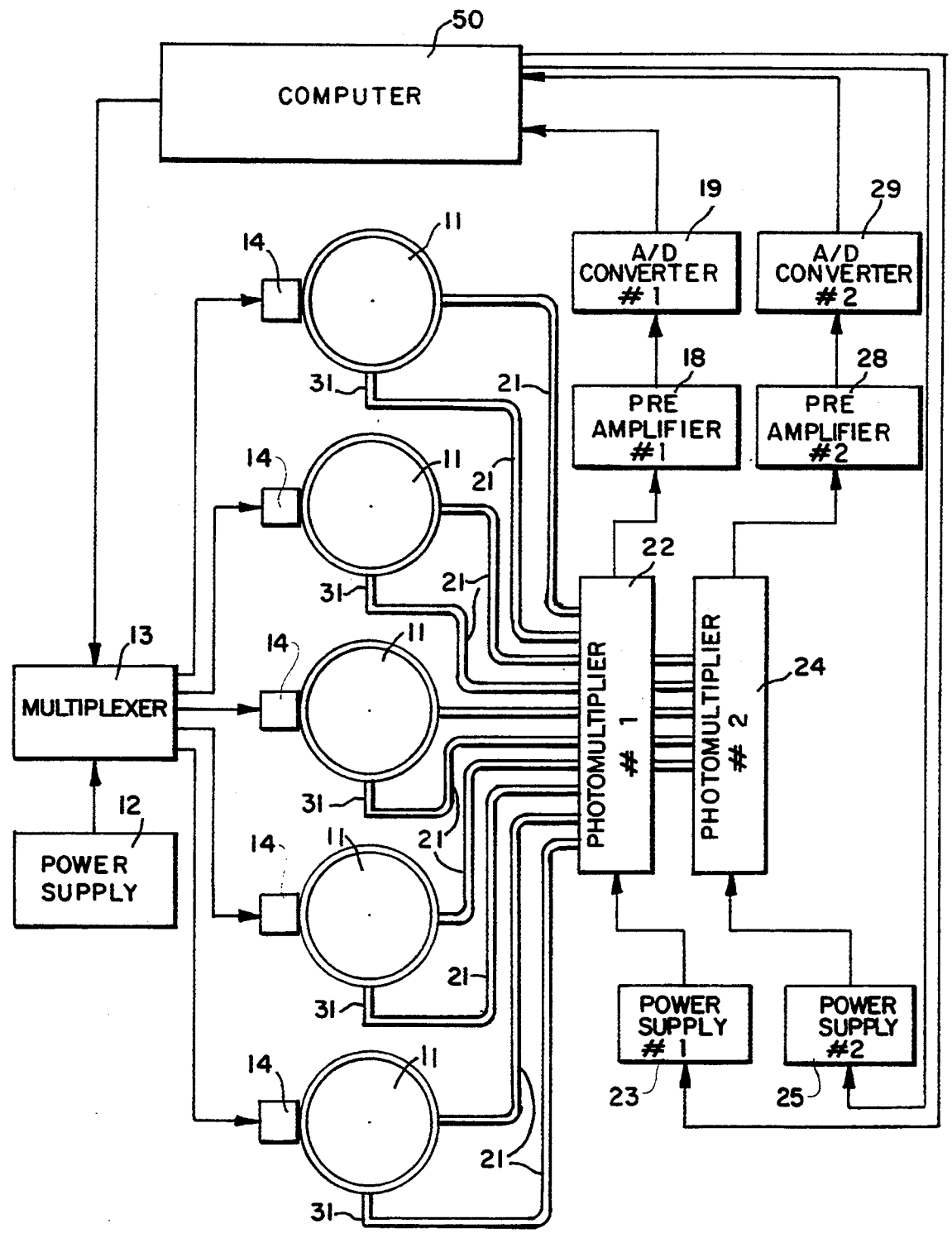
FIG. 2 illustrates another embodiment of the apparatus of the present invention that uses two fiber-optic light guide detectors on each sample vial.

A second embodiment of the apparatus of the present invention is shown in FIG. 2. In this embodiment two fiber-optic light guides 21,31 are arranged on each vial 11 to receive transmitted light instead of the two photodiode detectors 15,16 shown in FIG. 1. The positions of the light guides 11 are preferably the same as for the photodiodes 15,16 for the first embodiment described above, i.e., disposed 90° and 180° from the light source 14. All of the 180° light guides 21 are fed to a first large-area photomultiplier 22, the output of which is connected to the computer 50 via a first preamplifier 18 and a first analog-to-digital converter 19. All 90° light guides 31 are fed to a second large-area photomultiplier 24 the output of which is connected to the computer 50 via a second preamplifier 28 and a second analog-to-digital converter 29. Finally, each of the photomultipliers 22,24 is connected to its own high-voltage power supply 23,25. Both high-voltage power supplies 23,25 are separately controlled by the computer 50. Depending on the particular blood culture medium used, the light intensities at the 90° fiber-optic channel and at the 180° fiber-optic channel can be quite different. Therefore, it is advantageous if the gain in both the first and the second photomultiplier tubes 22,24 can be adjusted to the specific light intensity by controlling the high voltages separately. This adjustment is required to prevent photocurrent saturation artifacts within the photomultiplier. In certain embodiments of the present invention, it is preferred to control voltage in such a way that the amplified output photocurrent is held always at the same level. In this case, the resulting computer-controlled high voltage is the system output signal which reveals the received light intensity. On the one hand, this prevents any photocurrent saturation effects if the output current is stabilized at a reasonable low value, e.g., at 100 μA. On the other hand, the high voltage of a computer-controlled photomultiplier tube is logarithmically related to the light intensity. At an extreme light intensity, the computer reduces the photomultiplier tube ("pmt") high voltage. Because the photomultiplier tube gain changes rapidly with changing high voltage, only a relatively small voltage decrease, e.g. 100 V, is required to compensate for several orders of magnitude in light intensity increase. Therefore, the system shows an excellent dynamic range, and blood culture vials with high or low light output levels can be monitored without a need for any additional adjustment.

Those of ordinary skill will realize that the fiber-optic light guides 21,31 serve to receive the reemerging light and transmit it to the photomultipliers 22,24 that convert the signal received from the light guides into an analog signal that is proportional to intensity. This function is also accomplished by the photodiode detectors 15,16 described above, except that since the detectors create an analog signal directly, a demultiplexer 17 is used rather than the photomultipliers 22,24 shown in FIG. 2. Thus, in this embodiment, the demultiplexer 17 shown in FIG. 1 is not required, because only one light source 14 is operated at a time and the large-area photomultipliers 22,24 act as a parallel-processing device. In this embodiment, there is information within the computer 50 to identify the vial 14 from which the intensity data originates. The separation between the two positions of the light guides 21,31 is established and maintained by utilizing two identical signal channels, i.e., two photomultipliers 22,24, two preamplifiers 18,28, and two analog-to-digital converters 19,29.

Figure 3:
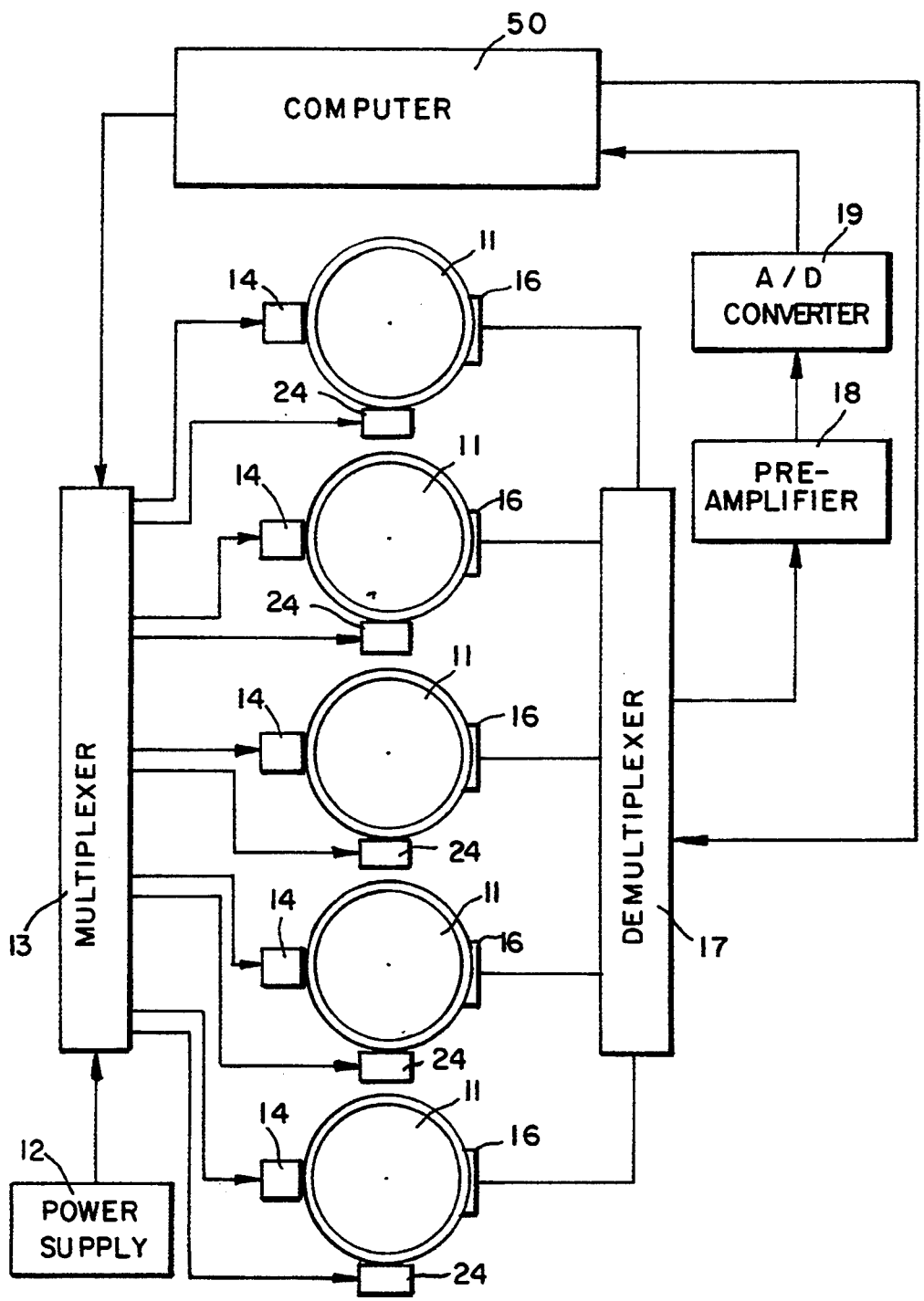
FIG. 3 is another embodiment of the apparatus of the present invention similar to that of FIG. 1 except two light sources and one photodiode detector are used.

Referring now to FIG. 3, a third embodiment of the apparatus of the present invention is shown. In this embodiment, two light sources 14,24 are disposed against each vial 11. A first light source 14 is placed in a first position and connected to a multiplexer 13, which is again connected to a power supply 12 and a computer 50 for controlling as described above with reference to FIGS. 1 and 2. However, in the embodiment illustrated in FIG. 3, a second light source 24 is also positioned against each vial 11. As shown, the second light source 24 is most preferably placed about 90° from the position of the first light source 14 and is also controlled by the multiplexer 13. A single photodiode detector 16 is disposed at a location preferably 180° from the first light source 14, as discussed above with reference to FIG. 1. In the embodiment of FIG. 3 however, since a single detector 16 is provided for each vial 11 a single detector output per vial 11 is transmitted to the demultiplexer 17, which is also controlled by the computer 50. As discussed above with reference to FIG. 1, the demultiplexer 17 produces a single analog output indicating the intensity of the light reemerging from each vial 11. This output is amplified by the preamplifier 18 and then converted to a digital signal by the analog to digital converter 19 prior to its being stored in the computer 50. The embodiment illustrated in FIG. 3 permits the determination of reemerging light intensities at points preferably spaced 90° and 180° from the source, as was the case with the embodiment of FIG. 1. However, the embodiment of FIG. 3 is less expensive since two light sources 14,24 and only a single photodiode detector 16 are required. At the present time, the preferred photodiode detectors 16 are significantly more expensive than the preferred light sources 14 referenced below. Thus, the embodiment of FIG. 3 will be less expensive to construct since half as many photodiode detectors are required. These savings are particularly significant when considered in terms of those embodiments of the present invention built to handle several hundred sample vials at one time.

Another alternative embodiment of the present invention would comprise a device wherein two light sources are placed against each vial, as illustrated in FIG. 3, but the photodiode detector is replaced by a single fiber-optic light guide, preferably the 180° light guide illustrated in FIG. 2. As discussed above with reference to FIG. 2, a photomultiplier and attendant power supply would be required to produce an output signal, in this embodiment, however, only a single channel is required. The output signal from the photomultiplier is amplified and digitized prior to being stored in the computer, as was the case with the embodiment of FIG. 2.

In any of these embodiments one preferred light source 14 would comprise a light emitting diode such as the Mitsubishi Cable Industries model DLZ1-RN30 ultra brightness red LED lamp which emits light at a wavelength at 670 nm. The preferred embodiments of the present invention can use any source that emits electromagnetic radiation at a wavelength between about 600–800 nm. One preferred large-area photodiode 15,16 is the Hamamatsu Model S1227-1010BR ceramic case silicon photodiode that has a 10 mm × 10 mm sensitive area although other similar types of photodiodes may also be used. For the embodiment illustrated in FIG. 2, a large-area photomultiplier such as the Hamamatsu Model R1513 head-on type is one example of a preferred device but, again, other photomultiplier tubes or devices that perform the same function could be used. Also, in these embodiments, the fiber-optic light guides 21,31 are preferably low-cost plastic products such as the jacketed optical grade light guide, type F2550, offered by Edmund Scientific or similar fibers which are otherwise widely available. In any embodiment, the blood culture vials 11, are of a well known type such as the standard BACTEC® vials and contain a standard BACTEC® aerobic or anaerobic medium all of which are both supplied by Becton Dickinson Diagnostic Instrument Systems, Sparks, Md., however, many other types of sample containers are also useful.

The present invention operates using the principle that when light enters a medium the photons are both scattered and absorbed, migrating along a path length that is usually greater than the straight line distance between the emitter and detector. As known to those of ordinary skill, light scattering measurement has been employed in the past for detection of biological activities in body fluids such as urine. In urine, however, the dominating process is scattering, while absorption can be almost neglected. In addition, the volume density of scattering centers in body liquids such as urine is relatively low and the effects of absorption can be accounted for. Therefore, single-event scattering dominates and it is possible to describe the path length of the migrating photons as a function of the external scattering angle. However, in blood cultures and other fluids with which the present invention could be used, a completely different situation exists. In most cases, the light absorption is so high that no reemerging light seems to be present at a first glance. Due to this high degree of absorption, light scattering in blood cultures was not used in the prior art for microorganism detection. Additionally, the volume density of scattering centers in blood cultures is also relatively high. Therefore, most photons experience multiple-scatterings and migrate along a complex set of path lengths. As a result, the properties of light reemerging from a blood culture medium cannot be characterized in terms of the external scattering angle, as is the case with urine. Instead, the light reemerging from blood cultures depends significantly on the relative locations of the emission position where light emerges to the light injection position where the light was introduced.

Thus, after the injection of light into a medium such as blood cultures, some photons enter the medium, are immediately scattered and emerge. Other photons migrate through the sample for some time before they reach the surface and emerge. Consequently, the photon path length within the medium cannot be described as a discrete one, but is instead a distribution of the path lengths of the individual photons. In measuring the intensity of the reemerging light, a probability function for escape, either for a single photon or for a plurality of photons, is therefore obtained. As will be understood by those of ordinary skill, the probability for escape depends on both the scattering coefficient, $\mu_S$, and the absorption coefficient, $\mu_A$. One would expect that detection of biological activities in a scattering and absorbing medium is possible if these activities have an impact on either $\mu_S$ or on $\mu_A$ or on both. It has now been found that the sensitivity of the detection of the photons is highly dependent upon the geometrical arrangement of the source and detectors.

In order to determine the optimum positions for the photodiodes 15,16 or the fiber-optic light guides 21,31 that collect the reemerging light in the apparatus described above, an equation describing the reflectance, R(r), at a distance, r, between light injection and emission for a semi-infinite scattering and absorbing medium is used. This equation has been developed in connection with quantitative reflectance spectroscopy for the non-invasive measurement of photosensitizer concentration in living tissue during photodynamic therapy. See M. S. Patterson et al., "Photodynamic Therapy: Mechanisms," SPIE Vol. 1065 (1989), at pp. 115–122, which is incorporated herein by reference. The reflectance, R(r), is given by:

$$R(r) = \frac{z_0}{2\pi} \frac{\exp[-\mu_{eff}(z_0^2 + r^2)^{\frac{1}{2}}]}{z_0^2 + r^2} \left[ \mu_{eff} + \frac{1}{(r^2 + z_0^2)^{\frac{1}{2}}} \right] \quad (1)$$

with $$z_0 = \frac{1}{\mu'_S} \quad (2)$$

$$\mu'_S = (1 - g)\mu_S \quad (3)$$

and $$\mu_{eff} = [3\mu_A(\mu_A + \mu'_S)]^{\frac{1}{2}} \quad (4)$$

In equation (3), $\mu'_S$ is the reduced scattering coefficient that takes into account the anisotropy factor, g, describing the angular scattering behavior for the particles. For large distances, i.e., for $r^2 >> z_0^2$, equation (1) can be written in the form:

$$R(r) = z_0 \frac{\exp[-\mu_{eff} r]}{2\pi r^2} \left[ \mu_{eff} + \frac{1}{r} \right] \quad (5)$$

and for back-scattering, i.e., for r=0, we obtain:

$$R(r=0) = \frac{\exp[-\mu_{eff}z_0]}{2\pi z_0} \left[ \mu_{eff} + \frac{1}{z_0} \right] \quad (6)$$

Absorption sensitivity, $S_A$, can be defined as:

$$S_A = \frac{dR/R}{d\mu_A/\mu_A} \quad (7)$$

and a scattering sensitivity, $S_S$, and be defined as:

$$S_S = \frac{dR/R}{d\mu_S/\mu_S} \quad (8)$$

Using equations (5) and (7), the absorption sensitivity at a large distance from the light injection area is therefore:

$$S_A(r) = \frac{3}{2} \mu_A(2\mu_A + \mu'_S) \frac{r}{\mu_{eff} + \frac{1}{r}} \quad (9)$$

Using equations (6) and (7), the absorption sensitivity in the back-scattering mode is:

$$S_A(r=0) = \frac{3}{2} \mu_A(2\mu_A + \mu'_S) \frac{z_0}{\mu_{eff} + \frac{1}{z_0}} \quad (10)$$

For typical blood cultures, $Z_0$ is on the order of one millimeter or less. Therefore, a comparison of equations (9) and (10) indicates that the absorption sensitivity can be improved significantly by using large distances between the light injection position and the emission position.

Using equations (5) and (8), and taking into account that $Z_0 = 1/\mu'_S$, one can calculate for the scattering sensitivity at a large distance from the light injection area:

$$S_S = 1 + \frac{3}{2} \mu_a\mu'_s \frac{r}{\mu_{eff} + \frac{1}{r}} \quad (11)$$

In contrast to equation (9) describing the absorption sensitivity, equation (11) includes a constant term, 1, which prevents the scattering sensitivity from becoming very small in the back-scattering mode. A calculation of $S_S(r=0)$ shows that changes in the scattering behavior can be monitored sensitively also in the back-scattering mode.

Since $S_A$ and $S_S$ depend in different ways on the distance between light injection and emission positions it is possible to separate the effects of absorption and scattering in blood culture media. This offers a chance to combine detection and partial identification within one instrument.

Figure 4:
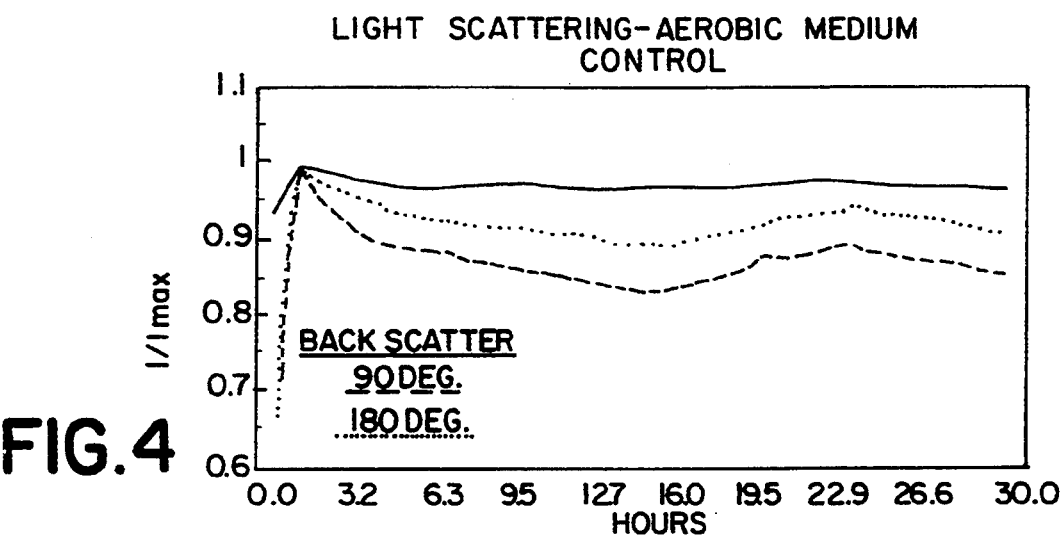
FIG. 4 is a plot obtained using apparatus made according to the present invention and a sample vial containing an aerobic medium and blood, but no microorganisms.

Referring to FIG. 4 there is shown a plot of intensity versus time obtained on an apparatus made according to the present invention and a standard BACTEC® vial containing a standard BACTEC® 26A aerobic medium from Becton Dickinson Diagnostic Instrument Systems, Sparks, Md., and containing 5 ml of blood, but no microorganisms. As can be seen, the intensity of the reemerging light is rather constant over time, after passing through some initial adaption processes within the first two hours. For comparison, this plot and all others shown herein contain a back-scattering signal measured by means of an additional photodetector mounted closely adjacent to the injection location.

Figure 5:
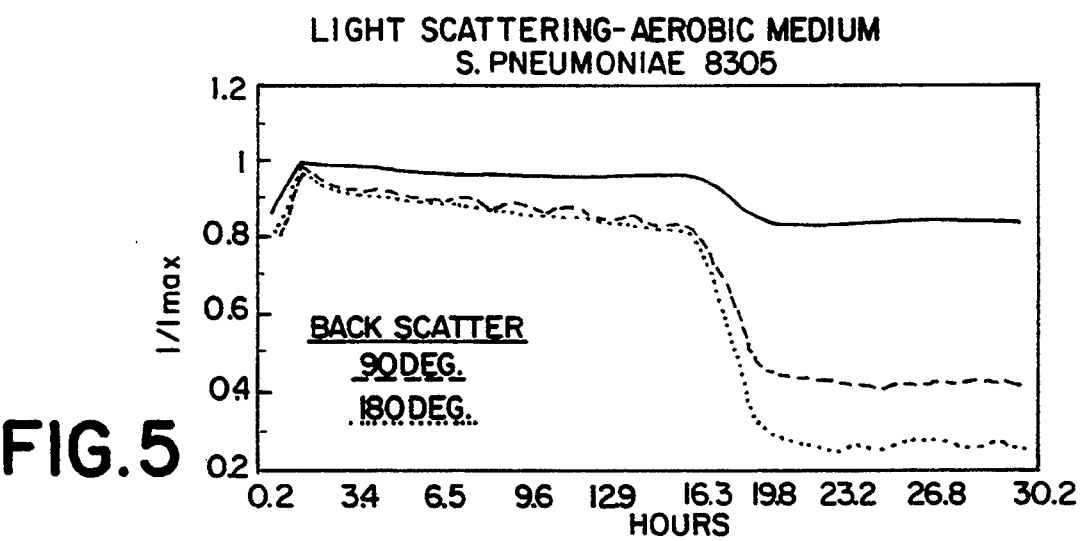
FIGS. 5–6 are plots obtained as described with reference to FIG. 4 wherein the vials also contained strains of microorganisms inoculated at a concentration of about 50 to 100 cfu/vial.
Figure 6:
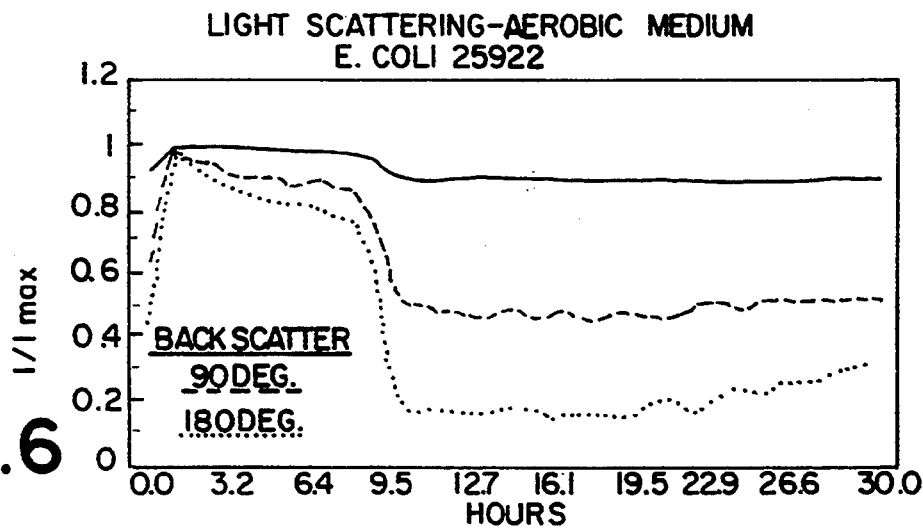

FIGS. 5-6 depict plots obtained on an apparatus made according to the present invention, using the BACTEC® vials containing the BACTEC® 26A aerobic medium referred to above and also containing 5 ml of blood and strains of microorganisms representing the species indicated on each Figure inoculated at a concentration of 50 to 100 cfu/vial. These plots illustrate that the detector at the largest distance responds most sensitively to bacterial growth. It can be seen that the 90° and 180° intensity values are relatively constant for a few hours, as was the case with the control shown in FIG. 4. However, for both the *S. pneumoniae* illustrated in FIG. 5 and the *E. coli* illustrated in FIG. 6, a dramatic drop in intensity level is eventually detected. As noted above, this drop is largest for the 180° detector and smaller for the 90° detector. It should be noted, however, that a detectable deflection occurs in even the backscatter intensity measurement, which is displaced approximately 0° from the emitter. These plots illustrate that bacteria are detected when a significant change in the intensity occurs. The relative magnitude of this change is related to the geometry between the emitter and the detector. Thus, it would be possible to construct a useful embodiment of the present invention that used a single emitter and a single detector. For example, the apparatus illustrated in FIG. 1 could be built except the 90° detectors 15 would be left out. Similarly, the embodiment of FIG. 2 could be constructed without the 90° fibers 31 and their associated photomultiplier 24 its preamplifier 28, A/D converter 29 and power supply 25. In either case, a device capable of detecting bacterial growth in accordance with the present invention would be provided. However, for reasons set forth below, such simplified embodiments are not the most preferred embodiments of the present invention because the relative data from two detectors, e.g., 90° and 180° can provide valuable data that can potentially be used to classify the type of bacteria detected.

Figure 7:
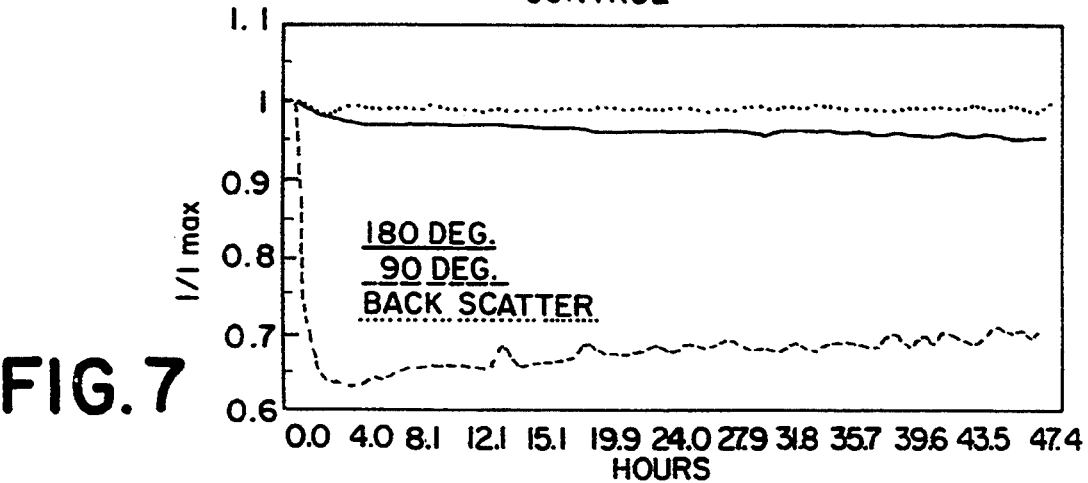
FIG. 7 is a plot obtained using apparatus made according to the present invention and a sample vial containing an anaerobic medium and blood, but no microorganisms.
Figure 8:
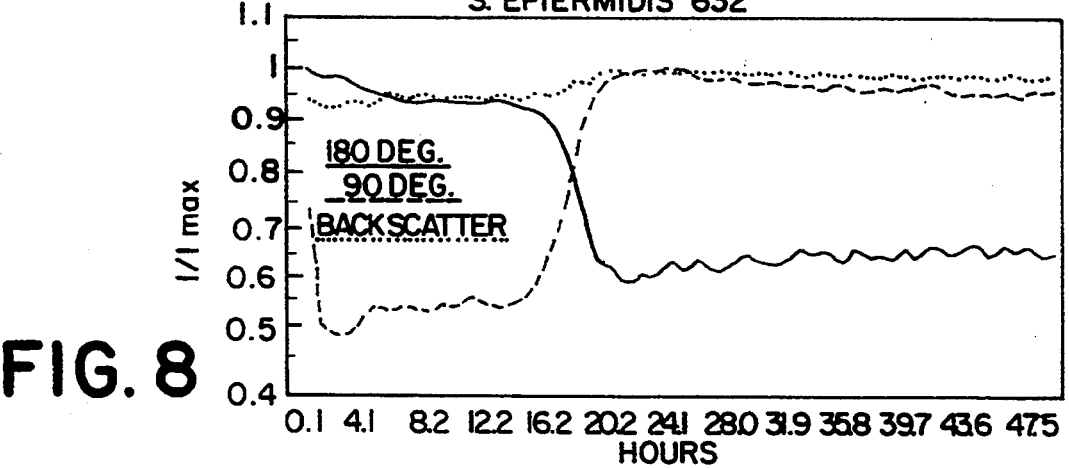
FIGS. 8–9 are normalized plots obtained as described with reference to FIG. 7 wherein the vials also contained strains of microorganisms inoculated at a concentration of about 50 to 100 cfu/vial.
Figure 9:
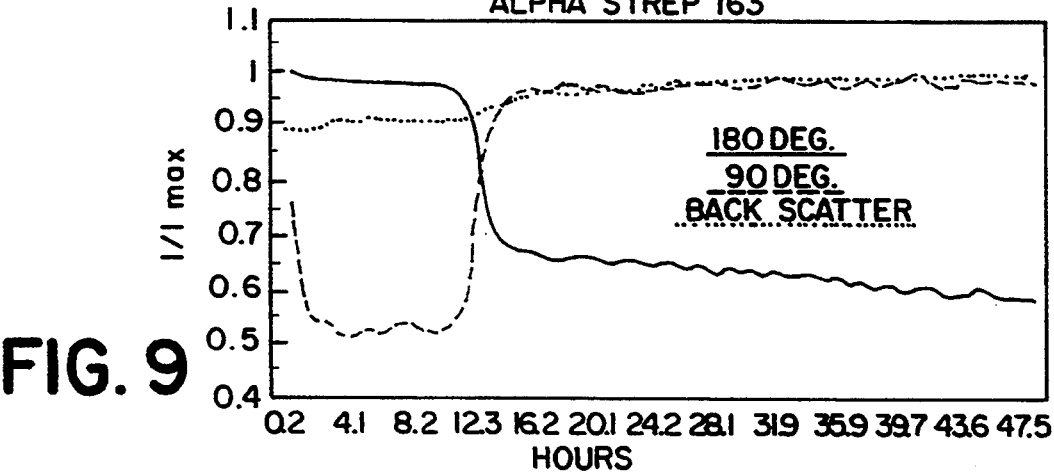

Thus, referring now to FIG. 7 there is shown a plot obtained using apparatus made according to the present invention, using a standard BACTEC® vial containing a BACTEC® Lytic anaerobic medium from Becton Dickinson Diagnostic Instrument Systems, Sparks, Md., that contains 5 ml of blood, but no microorganisms. As with the aerobic medium used in collecting the data illustrated in FIGS. 4-6, the reemerging light is rather constant over time after passing through some initial adaption processes within the first few hours. However, as seen in FIGS. 8-9 which are plots obtained on an apparatus made according to the present invention using vials containing a Lytic anaerobic medium, 5 ml of blood and strains of microorganisms representing the species indicated, inoculated at a concentration of 50 to 100 cfu/vial, the presence of bacteria is again reflected in a sharp change in intensity. These plots again illustrate that the detector at the largest distance, 180°, exhibits the largest change, while the detector at about seventy percent (0.707) of that distance, 90°, also responds very sensitively to bacterial growth, whereas the back-scattering detector, 0°, shows a much less pronounced but nonetheless detectable response.

It should be noted that unlike the plots seen in FIGS. 5-6, those shown in FIGS. 8-9 exhibit intensity curves for the 90° detector that are approximately symmetrically reversed from those of the 180° detector or the backscatter detector. The important result, however, is that in either the case of the 180° or 90° detector, a significant change in intensity occurred. The data shown in FIGS. 8–9 are normalized, thereby producing plots graphically similar to those of FIGS. 5–6. As discussed above, the variations between the 90° and 180° curves can be used to identify or at least classify the bacteria in the sample. Similar results would be obtained if spacings other than 90° and 180° were chosen.

The plots in FIGS. 4–9, therefore illustrate that biological activities within the blood culture medium, such as bacterial growth processes, result in a change in the reemerging light intensities. Therefore, biological activities such as bacterial growth can be detected by monitoring such reemerging light intensities. Because the photocurrent measurement per vial can be performed relatively fast, a very frequent measurement for each vial is possible. This allows for a short bacterial detection time. Since detectors located at different distances away from the light injection point respond in different ways, they are also utilized to perform partial identification of microorganisms.

Regarding partial identification, as data are collected using the present invention, a knowledge base will be established that will enable the users to both identify the presence of bacteria as well as characterize the type of bacteria. This latter aspect of the invention may be largely qualitative wherein those having proper experience "read" plots similar to those illustrated. The present invention will provide data, however, in a form that permits bacteria from a plurality of samples to be classified automatically by the type of bacteria present by providing a computer that has different types of characteristic plots stored in memory.

As will be readily understood by those of ordinary skill, the present invention discloses concepts that may be readily adapted or modified. For example, the samples in which bacterial activity is monitored may comprise fluids other than blood and may not necessarily include a culture medium. The specific embodiments set out in detail above have been provided for purposes of illustrating the invention, but are not limiting in nature. Reference should be made, therefore, to the appended claims in order to determine the scope of this invention.

What is claimed is:

1. A method for detecting biological activity within an absorptive sample held within a container comprising the steps of:
   injecting a first electromagnetic radiation into an absorptive sample at a first point located on a wall of a container from an electromagnetic radiation source disposed directly on the wall of the container to prevent backscatter radiation from the container being received by a detector;
   measuring a first radiation intensity value from the first electromagnetic radiation reemerging and being received by the detector at a second point located on the wall of the container;
   recording the first radiation intensity value; and
   repeating the steps of injecting, measuring and recording over a period of time,
   whereby biological activity is indicated by a marked change in the recorded first radiation intensity values.

2. The method of claim 1, further comprising the step of injecting a second electromagnetic radiation into the sample at a third point located on the wall of the container.

3. The method of claim 2, further comprising the steps of:
   measuring a second radiation intensity value from the second electromagnetic radiation reemerging at the second point located on the wall of the container; and
   partially identifying microorganisms within the sample by comparing the first radiation intensity value at the second point that corresponds to the injection at the first point with the second radiation intensity at the second point that corresponds to the injection at the third point.

4. A method for detecting biological activity within each of a plurality of absorptive samples, each sample being contained within one of a plurality of containers, wherein the biological activity within each sample is detected using the method of claim 2, and further comprising the steps of:
   multiplexing a source of electric power to a plurality of electromagnetic radiation sources, at least one each of which are disposed directly on or near a wall of one of a plurality of containers, each container containing one of a plurality of absorptive samples; and
   demultiplexing the first radiation intensity value corresponding to the sample in each of said plurality of containers to create an output signal.

5. A method for detecting biological activity within each of a plurality of absorptive samples, each sample being contained within one of a plurality of containers, wherein the biological activity within each sample is detected using the method of claim 2, and further comprising the step of multiplexing a source of electric power to a plurality of electromagnetic radiation sources, at least one each of which are disposed directly on or near a wall of one of a plurality of containers, each container containing one of a plurality of absorptive samples, wherein the step of measuring the first radiation intensity value comprises the steps of:
   collecting the first electromagnetic radiation reemerging from each sample; and
   transmitting the first electromagnetic radiation to means for converting the first electromagnetic radiation to the first radiation intensity value.

6. The method of claim 1, further comprising the step of measuring a second radiation intensity value from the first electromagnetic radiation reemerging at a third point located on the wall of the container.

7. The method of claim 6, further comprising the step of partially identifying microorganisms within the sample by comparing the first radiation intensity value measured at the second point with the second radiation intensity value measured at the third point.

8. A method for detecting biological activity within each of a plurality of absorptive samples, each sample being contained within one of a plurality of containers, wherein the biological activity within each sample is detected using the method of claim 6, and further comprising the steps of:
   multiplexing a source of electric power to a plurality of electromagnetic radiation sources, at least one each of which are disposed directly on or near a wall of one of a plurality of containers, each container containing one of a plurality of absorptive samples; and demultiplexing the first and second radiation intensity values corresponding to the sample in each of said plurality of containers to create an output signal.

9. A method for detecting biological activity within each of a plurality of absorptive samples, each sample being contained within one of a plurality of containers, wherein the biological activity within each sample is detected using the method of claim 6, and further comprising the step of multiplexing a source of electric power to a plurality of electromagnetic radiation sources, at least one each of which are disposed directly on or near a wall of one of a plurality of containers, each container containing one of a plurality of absorptive samples, wherein the steps of measuring the first and second radiation intensity values comprise the steps of:

collecting the first and second electromagnetic radiation reemerging from each sample; and transmitting the first and second electromagnetic radiation to means for converting the first and second electromagnetic radiation to the first and second radiation intensity values, respectively.

10. The method of claim 1, further comprising the step of measuring the backscatter intensity of the first electromagnetic radiation at a backscatter location adjacent the first point.

11. A method for detecting biological activity within each of a plurality of absorptive samples, each sample being contained within one of a plurality of containers, wherein the biological activity within each sample is detected using the method of claim 1, and further comprising the steps of:

multiplexing a source of electric power to a plurality of electromagnetic radiation sources, at least one each of which are disposed directly on or near a wall of one of a plurality of containers, each container containing one of a plurality of absorptive samples; and demultiplexing the first radiation intensity value corresponding to the sample in each of said plurality of containers to create an output signal.

12. A method for detecting biological activity within each of a plurality of absorptive samples, each sample being contained within one of a plurality of containers, wherein the biological activity within each sample is detected using the method of claim 1, and further comprising the step of multiplexing a source of electric power to a plurality of electromagnetic radiation sources, at least one each of which are disposed directly on or near a wall of one of a plurality of containers, each container containing one of a plurality of absorptive samples, wherein the step of measuring the first radiation intensity value comprises the steps of:

collecting the first electromagnetic radiation reemerging from each sample; and transmitting the first electromagnetic radiation to means for converting the first electromagnetic radiation to the first radiation intensity value.

13. The method of claim 1, further comprising the steps of:

amplifying the first radiation intensity value;

converting the first radiation intensity value into a digital signal; and storing the digital signal in a computer.

14. Apparatus for detecting biological activity within an absorptive sample held within a container comprising:

a light source disposed directly on a wall of a container for injecting a first electromagnetic radiation into an absorptive sample in the container at a first point located on the wall of the container and to prevent backscatter radiation from the container;

a detector disposed directly on the wall of the container for measuring a first radiation intensity value of the first electromagnetic radiation reemerging at a second point located on the wall of the container and to prevent said detector from receiving backscatter radiation from the container;

a controller for repeatedly activating said light source and said detector to measure the first radiation intensity values over a period of time; and a computer for recording the first radiation intensity values, whereby biological activity is indicated by a marked change in the recorded first radiation intensity values.

15. The apparatus of claim 14, further comprising a second detector for measuring a second radiation intensity value from the first electromagnetic radiation reemerging at a third point located on the wall of the container.

16. The apparatus of claim 14, further comprising a second light source for injecting a second electromagnetic radiation into the sample at a third point located on the wall of the container.

17. The apparatus of claim 14, further comprising a backscatter detector for measuring the backscatter intensity of the first electromagnetic radiation at a location adjacent the first point.

18. The apparatus of claim 14, further comprising a multiplexer for sequentially activating each of a plurality of light sources disposed adjacent a plurality of samples; and a demultiplexer for identifying the intensity value corresponding to each sample to create an output signal.

19. The apparatus of claim 14, further comprising a multiplexer for sequentially activating each of a plurality of light sources disposed adjacent a plurality of samples, and wherein the detector comprises;

a light guide for collecting the electromagnetic radiation reemerging from the sample; and a photomultiplier tube for converting the electromagnetic radiation to an intensity value, the photomultiplier tube being connected to the light guide.

20. The apparatus of claim 19 further comprising a second detector for measuring an intensity value of the electromagnetic radiation at a third point located on each of the plurality of containers, wherein the second detector comprises:

a second light guide for collecting the electromagnetic radiation reemerging from the sample at the third point; and a second photomultiplier tube for converting the electromagnetic radiation to an intensity value, the photomultiplier tube being connected to the second light guide.

21. The apparatus of claim 14 wherein the light source emits light at a wavelength between about 600 nm and 800 nm.

* * * * *